United States Patent
Watanabe et al.

(10) Patent No.: US 8,462,337 B2
(45) Date of Patent: Jun. 11, 2013

(54) SPECTROMETER, SPECTROMETRY, AND SPECTROMETRY PROGRAM

(75) Inventors: Motoyuki Watanabe, Hamamatsu (JP); Kazuya Iguchi, Hamamatsu (JP); Kengo Suzuki, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 183 days.

(21) Appl. No.: 13/141,152

(22) PCT Filed: Sep. 8, 2009

(86) PCT No.: PCT/JP2009/065660
§ 371 (c)(1),
(2), (4) Date: Jun. 21, 2011

(87) PCT Pub. No.: WO2010/073778
PCT Pub. Date: Jul. 1, 2010

(65) Prior Publication Data
US 2011/0255085 A1    Oct. 20, 2011

(30) Foreign Application Priority Data

Dec. 25, 2008    (JP) ................................. 2008-330349

(51) Int. Cl.
*G01J 1/04* (2006.01)
*G01J 3/30* (2006.01)

(52) U.S. Cl.
USPC ...................... 356/317; 356/236; 250/363.01

(58) Field of Classification Search
USPC ..................... 356/317, 236; 250/363.01, 368, 250/484.2
See application file for complete search history.

(56) References Cited

U.S. PATENT DOCUMENTS

| | | | |
|---|---|---|---|
| 2009/0127450 A1 | 5/2009 | Bleuse et al. | |
| 2010/0102238 A1* | 4/2010 | Kanazawa et al. | 250/363.01 |
| 2011/0098962 A1* | 4/2011 | Iguchi et al. | 702/104 |

FOREIGN PATENT DOCUMENTS

| | | |
|---|---|---|
| JP | 5-60613 | 3/1993 |
| JP | 5-72039 | 3/1993 |
| JP | 9-292281 | 11/1997 |
| JP | 10-73486 | 3/1998 |
| JP | 11-30552 | 2/1999 |
| JP | 3287775 | 3/2002 |
| JP | 2003-215041 | 7/2003 |
| JP | 2004-309323 | 11/2004 |
| JP | 2006-292511 | 10/2006 |
| JP | 2007-33334 | 2/2007 |

(Continued)

*Primary Examiner* — Layla Lauchman
(74) *Attorney, Agent, or Firm* — Drinker Biddle & Reath LLP

(57) ABSTRACT

A spectroscopic measurement apparatus 1A comprises an integrating sphere 20 in which a sample S is located, a spectroscopic analyzer 30 dispersing the light to be measured from the sample S and obtaining a wavelength spectrum, and a data analyzer 50. The analyzer 50 includes an object range setting section which sets a first object range corresponding to excitation light and a second object range corresponding to light emission from the sample S in a wavelength spectrum, and a sample information analyzing section which determines a luminescence quantum yield of the sample S, determines a measurement value $\Phi_0$ of the luminescence quantum yield from results of a reference measurement and a sample measurement, and determines, by using factors $\beta$, $\gamma$ regarding stray light in the reference measurement, an analysis value $\Phi$ of the luminescence quantum yield with the effect of stray light reduced by $\Phi = \beta\Phi_0 + \gamma$. This realizes a spectroscopic measurement apparatus, a measurement method, and a measurement program which can reduce the effect of stray light generated in a spectrometer.

6 Claims, 12 Drawing Sheets

FOREIGN PATENT DOCUMENTS

| JP | 2007-86031 | 4/2007 |
| JP | 2008-70172 | 3/2008 |
| JP | 2008-518222 | 5/2008 |
| WO | WO 2006/092475 | 9/2006 |

* cited by examiner

SPECTROMETER, SPECTROMETRY, AND SPECTROMETRY PROGRAM

TECHNICAL FIELD

The present invention relates to a spectroscopic measurement apparatus having an integrating sphere, a spectroscopic measurement method to be performed by using the spectroscopic measurement apparatus, and a spectroscopic measurement program.

BACKGROUND ART

An integrating sphere is used to measure the intensity of light emitted from a sample. The inner wall of the integrating sphere is made out of a coating or a material having a high reflectance and excellent in diffuseness, and light incident on the inner wall surface is multi-diffusely-reflected. Then, the diffused light from the sample enters a photodetector through an exit aperture provided at a predetermined position of the integrating sphere to be detected, and this method can obtain information of light emitting intensity and the like of the sample with high accuracy without depending on a light emission pattern, a light emission angle characteristic, and the like of the sample (for example, refer to Patent Documents 1 to 3).

An organic EL (electroluminescence) element serves as an example of the sample of a target of measurement using the integrating sphere. The organic EL element is a light emitting element generally having a structure with an anode, an organic layer including a light emitting layer, and a cathode laminated on a substrate made out of glass or a transparent resin material. Photons are generated by holes injected from the anode and electrons injected from the cathode being recombined in the light emitting layer, and the light emitting layer emits light.

In measurement and evaluation of light emission characteristics of the organic EL element, an external quantum efficiency defined by a ratio of the number of photons emitted to the outside of the element to the number of injected electrons, and the like, becomes important. Further, in measurement and evaluation of a luminescent material used in the organic EL element, a luminescence quantum yield (internal quantum efficiency) defined by a ratio of the number of photons of light emitted from the sample to the number of photons of excitation light absorbed by the sample becomes important. A light measurement device using the integrating sphere can be preferably used for evaluation of quantum efficiency of such an organic EL element.

CITATION LIST

Patent Literature

Patent Document 1: Japanese Patent Publication No. 3287775
Patent Document 2: Japanese Patent Application Laid-Open No. 2007-33334
Patent Document 3: Japanese Patent Application Laid-Open No. 2007-86031
Patent Document 4: Japanese Patent Application Laid-Open No. H11-30552
Patent Document 5: Japanese Patent Application Laid-Open No. H5-60613

SUMMARY OF INVENTION

Technical Problem

In recent years, the importance of evaluating the luminescence quantum yield of a luminescent material used for light emitting elements has been increased to improve a light emitting efficiency of a light emitting element such as an organic EL element in terms of power consumption reductions, in research and development of next-generation displays and next-generation illumination. As the evaluation method of the luminescence quantum yield, there is a method for measuring an absolute luminescence quantum yield of a luminescent material by a photoluminescence (PL) method with a light measurement device having the above-described integrating sphere.

Specifically, in the evaluation of the luminescence quantum yield by the PL method, a sample of a luminescent material located in the integrating sphere is irradiated with excitation light of a predetermined wavelength, and a luminescence quantum yield defined by a ratio of the number of photons of light emission from the sample to the number of photons of the excitation light absorbed by the sample is measured. In this case, the light emission from the sample is, for example, fluorescence to be emitted from the sample excited by irradiation with excitation light, and generally, results in light of a longer wavelength than that of the excitation light. Further, in detection of light to be measured emitted from the integrating sphere, by using a configuration for measuring a wavelength spectrum of the light to be measured with a spectrometer, the excitation light and the light emission from the sample can be separately measured (refer to Patent Document 1).

Here, in the quantum yield measurement of the sample described above, various types of samples serve as measurement objects, such as, for example, a sample that does not allow a prolonged time of irradiation with excitation light due to the effect of oxygen and the like. Accordingly, in the quantum yield measurement using a spectrometer, a configuration using a multi-channel type spectrometer capable of simultaneously performing measurement in the entire wavelength range that requires measurement is more suitable than a configuration for scanning a measurement wavelength while varying the configuration of the spectrometer by motor drive or the like with excitation light irradiated.

However, in a spectroscopic measurement apparatus using such a multi-channel spectrometer, relatively much stray light is generated due to the structure of the spectrometer and the like, and there is a problem of the effect of stray light on measurement results (refer to Patent Documents 4 and 5). For example, in a measurement of the luminescence quantum yield that is performed by irradiating a sample in an integrating sphere with excitation light, when the excitation light enters the spectrometer, stray light is generated due to diffused reflection and the like of the excitation light inside thereof. Such stray light due to excitation light can cause, by being erroneously detected as a wavelength component other than the excitation light, a reduction in the accuracy of the luminescence quantum yield to be determined from the measurement results.

The present invention has been made in order to solve the above-described problem, and an object thereof is to provide a spectroscopic measurement apparatus, a spectroscopic measurement method, and a spectroscopic measurement program which can reduce the effect of stray light generated in a spectrometer.

Solution to Problem

In order to achieve the above object, a spectroscopic measurement apparatus according to the present invention comprises: (1) an integrating sphere in which a sample as a measurement object is located, and having an entrance aperture for inputting excitation light with which the sample is irradiated, and an exit aperture for outputting light to be measured from the sample; (2) spectroscopic means dispersing the light to be measured output from the exit aperture of the integrating sphere and obtaining a wavelength spectrum; and (3) data analyzing means performing data analysis of the wavelength spectrum obtained by the spectroscopic means, and (4) the data analyzing means includes: object range setting means setting, of an entire measurement wavelength range in the wavelength spectrum, a first object range corresponding to the excitation light and a second object range which is a wavelength range corresponding to light emission from the sample and different from the first object range; and sample information analyzing means determining a luminescence quantum yield of the sample by analyzing the wavelength spectrum in a wavelength range including the first object range and the second object range, wherein (5) the sample information analyzing means, when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$, determines a measurement value $\Phi_0$ of the luminescence quantum yield by:

$$\Phi_0 = (I_{S2} - I_{R2})/(I_{R1} - I_{S1}),$$

defines factors $\beta$, $\gamma$ regarding stray light in the reference measurement as:

$$\beta = I_{R1}/I_{R0}$$

$$\gamma = I_{R2}/I_{R0}, \text{ and}$$

determines an analysis value $\Phi$ of the luminescence quantum yield by:

$$\Phi = \beta\Phi_0 + \gamma.$$

Further, a spectroscopic measurement method according to the present invention uses a spectroscopic measurement apparatus including (1) an integrating sphere in which a sample as a measurement object is located, and having an entrance aperture for inputting excitation light with which the sample is irradiated, and an exit aperture for outputting light to be measured from the sample, and (2) spectroscopic means dispersing the light to be measured output from the exit aperture of the integrating sphere and obtaining a wavelength spectrum, (3) for performing data analysis of the wavelength spectrum obtained by the spectroscopic means, and the spectroscopic measurement method (4) comprises: an object range setting step of setting, of an entire measurement wavelength range in the wavelength spectrum, a first object range corresponding to the excitation light and a second object range which is a wavelength range corresponding to light emission from the sample and different from the first object range; and a sample information analyzing step of determining a luminescence quantum yield of the sample by analyzing the wavelength spectrum in a wavelength range including the first object range and the second object range, wherein (5) the sample information analyzing step, when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$, determines a measurement value $\Phi_0$ of the luminescence quantum yield by:

$$\Phi_0 = (I_{S2} - I_{R2})/(I_{R1} - I_{S1}),$$

defines factors $\beta$, $\gamma$ regarding stray light in the reference measurement as:

$$\beta = I_{R1}/I_{R0}$$

$$\gamma = I_{R2}/I_{R0}, \text{ and}$$

determines an analysis value $\Phi$ of the luminescence quantum yield by:

$$\Phi = \beta\Phi_0 + \gamma.$$

Further, a spectroscopic measurement program according to the present invention is applied to a spectroscopic measurement apparatus including (1) an integrating sphere in which a sample as a measurement object is located, and having an entrance aperture for inputting excitation light with which the sample is irradiated, and an exit aperture for outputting light to be measured from the sample, and (2) spectroscopic means dispersing the light to be measured output from the exit aperture of the integrating sphere and obtaining a wavelength spectrum, (3) for making a computer execute data analysis of the wavelength spectrum obtained by the spectroscopic means, and the program (4) makes the computer execute: an object range setting process of setting, of an entire measurement wavelength range in the wavelength spectrum, a first object range corresponding to the excitation light and a second object range which is a wavelength range corresponding to light emission from the sample and different from the first object range; and a sample information analyzing process of determining a luminescence quantum yield of the sample by analyzing the wavelength spectrum in a wavelength range including the first object range and the second object range, wherein (5) the sample information analyzing process, when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$, determines a measurement value $\Phi_0$ of the luminescence quantum yield by:

$$\Phi_0 = (I_{S2} - I_{R2})/(I_{R1} - I_{S1}),$$

defines factors β, γ regarding stray light in the reference measurement as:

$$\beta = I_{R1}/I_{R0}$$

$$\gamma = I_{R2}/I_{R0}, \text{ and}$$

determines an analysis value Φ of the luminescence quantum yield by:

$$\Phi = \beta\Phi_0 + \gamma.$$

In the spectroscopic measurement apparatus, the measurement method, and the measurement program described above, the spectroscopic measurement apparatus is configured by using the integrating sphere which has the aperture for entrance of the excitation light and the aperture for exit of the light to be measured and is configured so as to be capable of measurement by the PL method, and the spectroscopic means which performs spectroscopic measurement of the light to be measured so that the excitation light and the light emission from the sample can be separated by the wavelength spectrum.

Then, in analysis of sample information using the wavelength spectrum, the results of two times of measurement of the reference measurement without the sample and the sample measurement with the sample are used, and for the measurement value $\Phi_0$ of the luminescence quantum yield, the factors β, γ regarding stray light are defined from the results of the reference measurement as in the above, and the analysis value Φ of the luminescence quantum yield is determined by using these factors by the calculation formula $\Phi = \beta\Phi_0 + \gamma$. In accordance with such a configuration, by correcting the measurement value $\Phi_0$ with the above-described formula, and determining the analysis value Φ corresponding to the true value of the luminescence quantum yield, it becomes possible to reliably reduce the effect of stray light in the spectrometer contained in the measurement results.

Here, it is preferable that the spectroscopic means for obtaining a wavelength spectrum of light to be measured includes a spectrometer for dispersing the light to be measured into wavelength components and a photodetector having detecting sections of multi-channels for detecting respective wavelength components of the light to be measured dispersed by the spectrometer, and is configured as a multi-channel spectrometer. In the configuration using a multi-channel spectrometer, relatively much stray light is generated as mentioned above, but in accordance with the method of determining the analysis value Φ corrected by the factors β, γ, even in such a configuration, the luminescence quantum yield with the reduced effect of stray light can be preferably determined. Further, such a method can also be likewise effectively applied when a spectrometer other than a multi-channel spectrometer is used.

Advantageous Effects of Invention

In accordance with the spectroscopic measurement apparatus, the spectroscopic measurement method, and the spectroscopic measurement program of the present invention, the spectroscopic measurement apparatus is configured by using the integrating sphere and the spectroscopic means which performs spectroscopic measurement of the light to be measured for obtaining a wavelength spectrum, in analysis of sample information, the results of two times of measurement of the reference measurement and the sample measurement are used, and for the measurement value $\Phi_0$ of the luminescence quantum yield, the factors β, γ regarding stray light are defined from the results of the reference measurement, and the analysis value Φ equal to the true value of the luminescence quantum yield is determined by the correction formula $\Phi = \beta\Phi_0 + \gamma$, and this allows reliably reducing the effect of stray light in the spectrometer contained in the measurement results.

DESCRIPTION OF EMBODIMENTS

Figure 1:
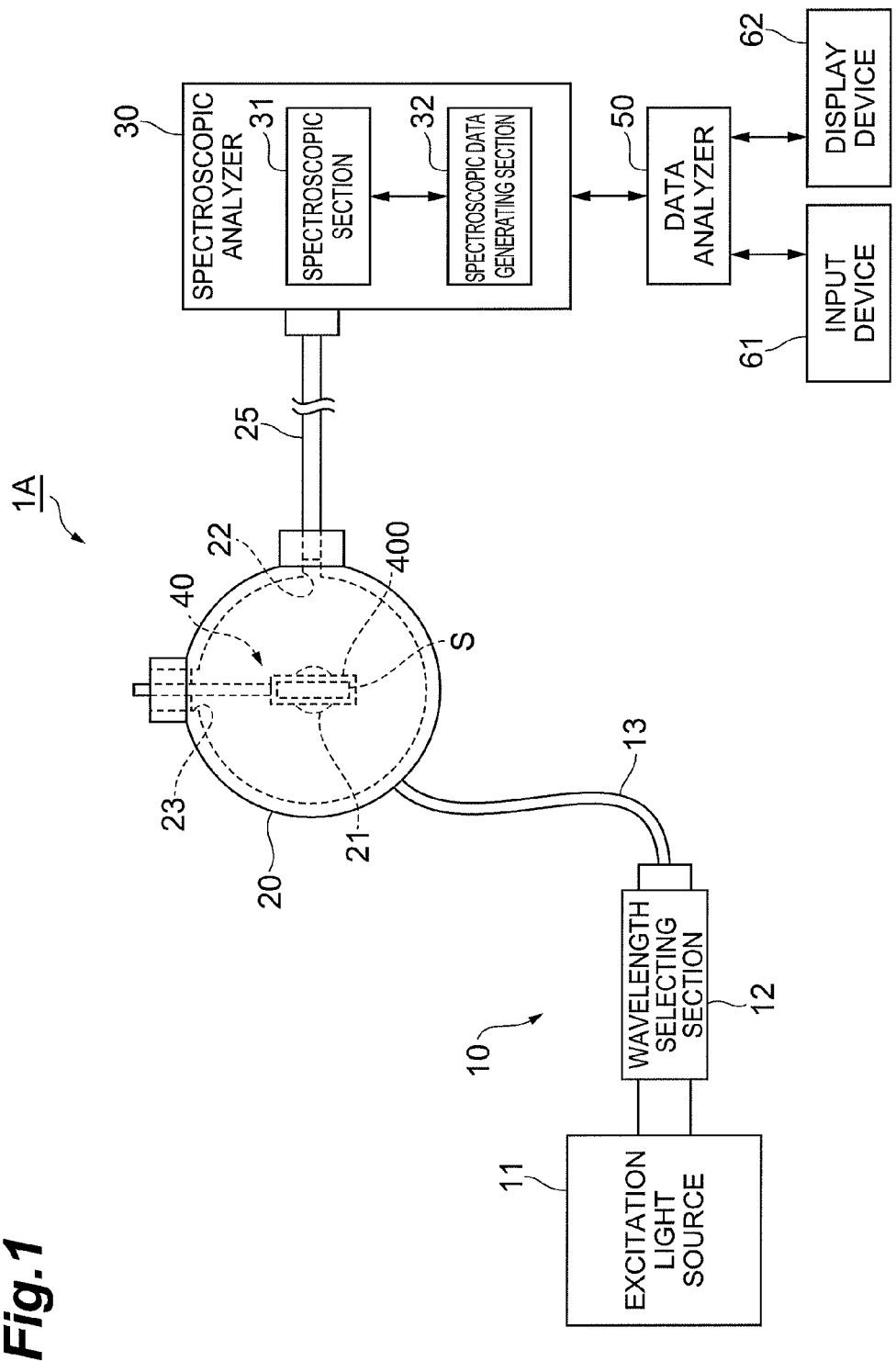
FIG. 1 is a diagram schematically showing a configuration of an embodiment of a spectroscopic measurement apparatus.

Hereinafter, preferred embodiments of a spectroscopic measurement apparatus, a spectroscopic measurement method, and a spectroscopic measurement program according to the present invention will be described in detail with reference to the drawings. In the description of the drawings, the same components are attached with the same reference symbols, and overlapping description will be omitted. Moreover, the dimensional ratios in the drawings are not always equal to those in the description.

FIG. 1 is a diagram schematically showing a configuration of an embodiment of a spectroscopic measurement apparatus. A spectroscopic measurement apparatus 1A in accordance with the present embodiment includes an excitation light supplying section 10, an integrating sphere 20, a spectroscopic analyzer 30, and a data analyzer 50, and is configured so as to irradiate a sample S such as a luminescent material with excitation light of a predetermined wavelength, and to enable measurement and evaluation of light emission characteristics such as fluorescence characteristics of the sample S by a photoluminescence method (PL method).

The excitation light supplying section 10 is excitation light supplying means which supplies the excitation light for measuring light emission characteristics of the sample S to the sample S of a measurement object housed in the integrating sphere 20. In the configuration example shown in FIG. 1, the excitation light supplying section 10 includes an excitation light source 11, and a light guide 13 for guiding light from the light source 11 to the integrating sphere 20. Further, a wavelength selecting section 12 for selecting a wavelength component of light to be used as excitation light is provided between the excitation light source 11 and the light guide 13. As such a wavelength selecting section 12, for example, a spectrometer can be used. Here, the wavelength selecting section 12 may not be provided, if it is unnecessary. Further, the wavelength of excitation light may be variably switched in the wavelength selecting section 12.

The integrating sphere 20 is an element used for measurement of the light emission characteristics of the sample S located interior, and has an entrance aperture 21 for inputting the excitation light with which the sample S is irradiated into the integrating sphere 20, an exit aperture 22 for outputting the light to be measured from the sample S to the outside, and a sample introduction opening 23 for carrying the sample S to the inside of the integrating sphere 20. A sample holder 40 is fixed to the sample introduction opening 23. Further, a sample container (sample cell) 400 for holding the sample S at a predetermined position in the integrating sphere 20 is provided at the end portion of the sample holder 40.

An output end portion of the light guide 13 for excitation light input is fixed to the entrance aperture 21 of the integrating sphere 20. For example, an optical fiber can be used as the light guide 13. Further, an input end portion of a light guide 25 for guiding the light to be measured from the sample S to the spectroscopic analyzer 30 in the subsequent stage is fixed to the exit aperture 22 of the integrating sphere 20. For example, a single fiber or a bundle fiber can be used as the light guide 25.

The spectroscopic analyzer 30 is spectroscopic means for dispersing the light to be measured from the sample S exiting through the light guide 25 from the exit aperture 22 of the integrating sphere 20 and for obtaining its wavelength spectrum. In this configuration example, the spectroscopic analyzer 30 is configured with a spectroscopic section 31 and a spectroscopic data generating section 32.

The spectroscopic section 31 includes a spectrometer for dispersing the light to be measured into wavelength components and a photodetector having detecting sections of multi-channels (e.g. 1024 channels) for detecting respective wavelength components of the light to be measured dispersed by the spectrometer into wavelength components, and is configured as a multi-channel spectrometer. For example, a CCD linear sensor with pixels of multi-channels arranged in one dimension can be specifically used as the photodetector. The entire measurement wavelength range where a wavelength spectrum is obtained by the spectroscopic section 31 can be set suitably in accordance with a specific configuration and the like, and for example can be set to 200 nm to 950 nm. Further, the spectroscopic data generating section 32 is spectroscopic data generating means which performs signal processing necessary for detection signals output from the respective channels of photodetector of the spectroscopic section 31 and generates wavelength spectrum data of the dispersed light to be measured. The wavelength spectrum data generated and obtained in the spectroscopic data generating section 32 are output to a data analyzer 50 of the subsequent stage.

The data analyzer 50 is data analyzing means which performs necessary data analysis for the wavelength spectrum obtained by the spectroscopic analyzer 30, to obtain information about the sample S. The specific content of the data analysis in the analyzer 50 is described later. Further, an input device 61 used for inputting instructions about data analysis and the like, inputting analysis conditions, and the like, and a display device 62 used for displaying data analysis results, and the like, are connected to the data analyzer 50.

Figure 2:
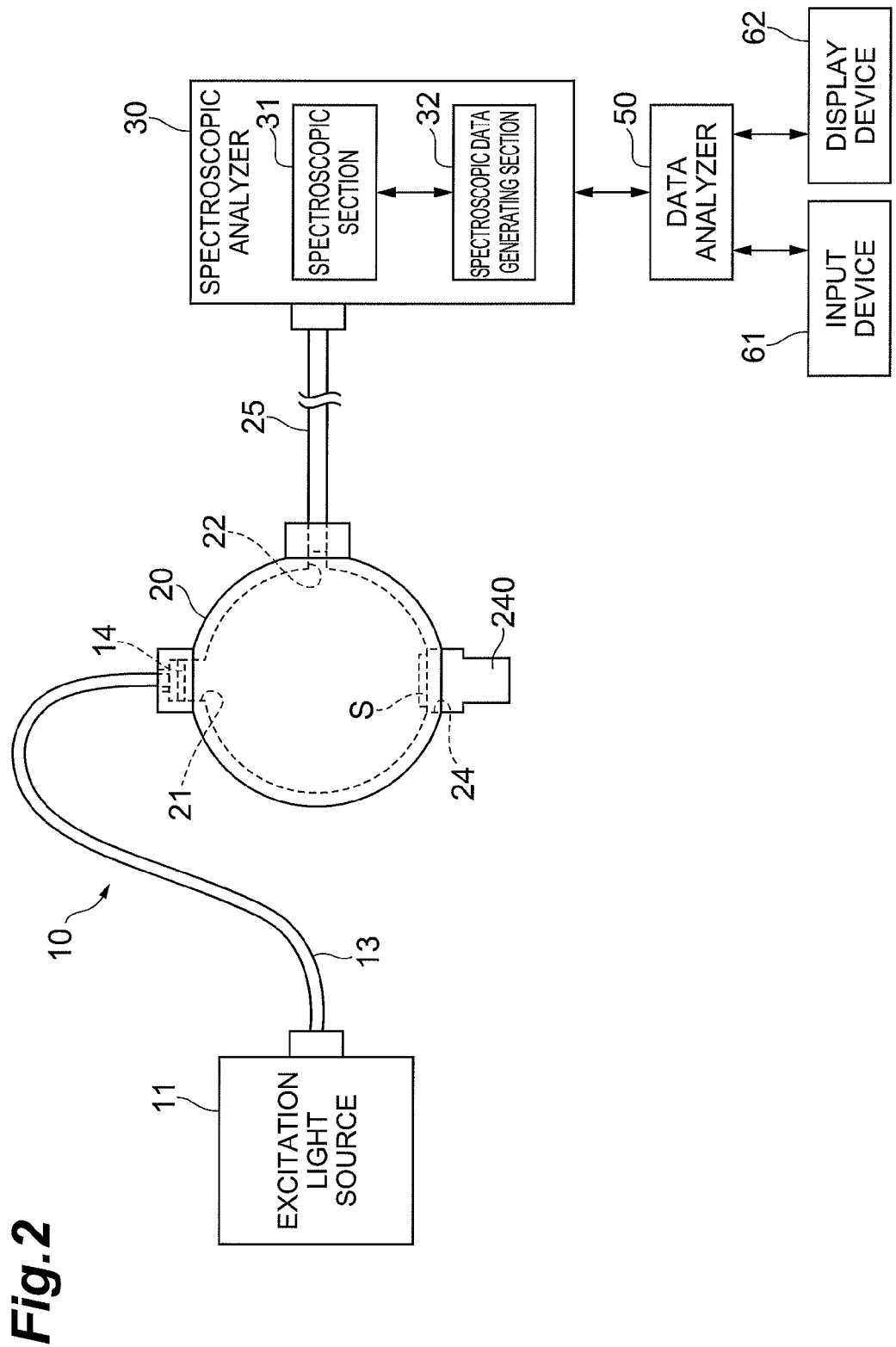
FIG. 2 is a diagram schematically showing a configuration of another embodiment of a spectroscopic measurement apparatus.

Here, various configurations other than the configuration shown in FIG. 1 can be specifically used for a configuration of the excitation light supplying section 10, the integrating sphere 20, and the like. FIG. 2 is a diagram showing a configuration of another embodiment of a spectroscopic measurement apparatus. In the modification example shown in FIG. 2, the excitation light supplying section 10 includes the excitation light source 11, the light guide 13, and an optical filter 14 such as an interference filter for selecting a predetermined wavelength component out of the light from the excitation light source 11 to use as excitation light with which the sample S is irradiated. Further, the integrating sphere 20 has the entrance aperture 21, the exit aperture 22, and a sample introduction opening 24. Further, in this configuration example, a sample holder 240 is fixed to the sample introduction opening 24, and the sample S is set on this sample holder 240.

Figure 3:
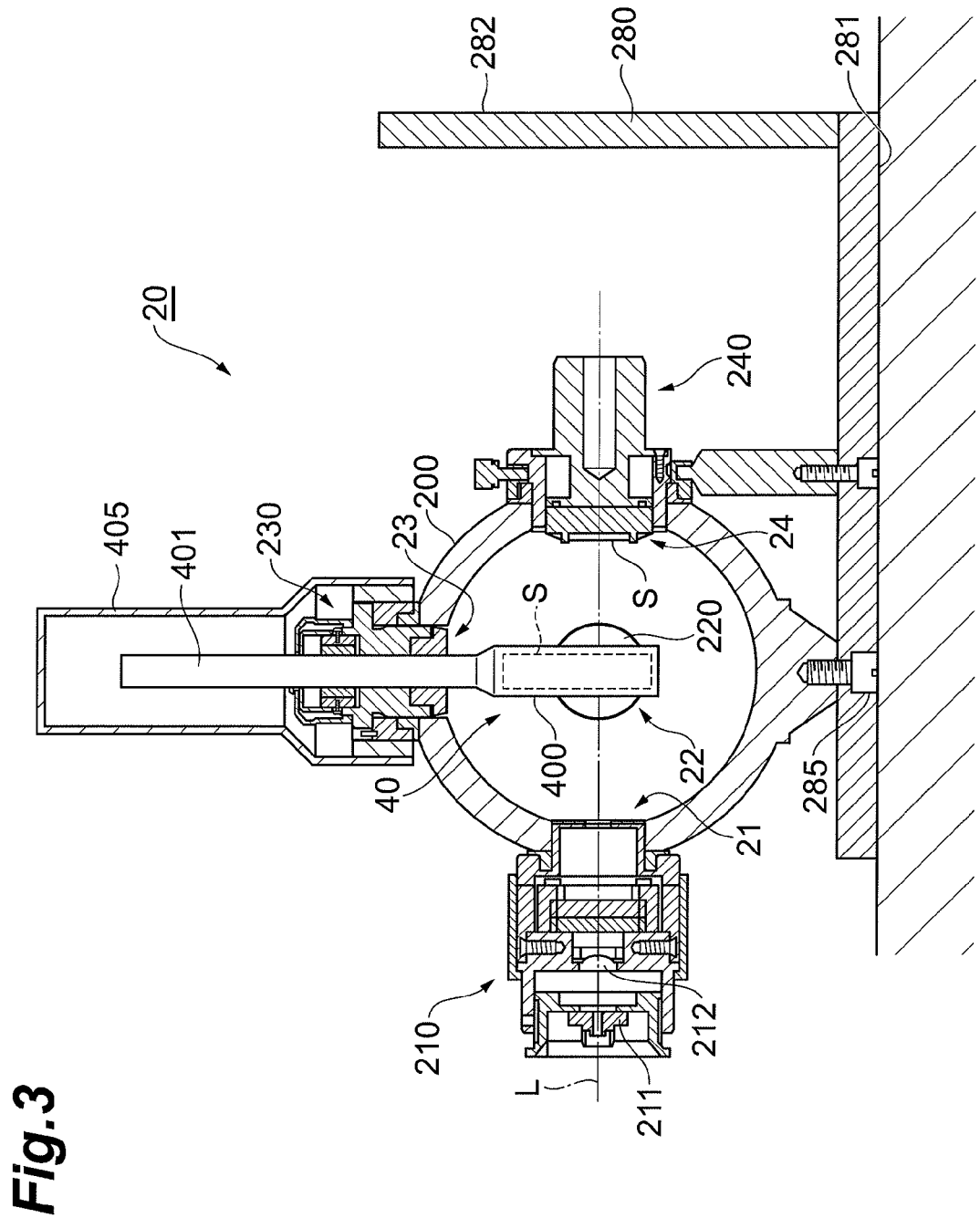
FIG. 3 is a sectional view showing an example of a configuration of the integrating sphere.

FIG. 3 is a sectional view showing an example of a configuration of the integrating sphere 20 used in the spectroscopic measurement apparatus 1A shown in FIG. 1, and shows a sectional structure of the integrating sphere 20 along an irradiation optical axis L of the excitation light. The integrating sphere 20 in this configuration example has an integrating sphere body 200 fixed to a mount 280 with an attachment screw 285. Further, the mount 280 is formed in an L-shape having two ground contact surfaces 281, 282 orthogonally intersecting each other. The irradiation optical axis L passes the center position of the integrating sphere body 200, and extends in a direction parallel to the ground contact surface 281 and orthogonal to the ground contact surface 282.

The entrance aperture 21, the exit aperture 22, and the sample introduction opening 23, which are shown in FIG. 1, are provided in the integrating sphere body 200. The entrance aperture 21 is provided at a predetermined position of the integrating sphere body 200 on one side of the optical axis L. Further, the exit aperture 22 is provided at a predetermined position on a plane which passes the center position of the integrating sphere body 200 and is orthogonal to the optical axis L. Further, the sample introduction opening 23 is provided on a plane which passes the center position of the integrating sphere body 200 and is orthogonal to the optical axis L, and at a position which is off by 90° from the exit aperture 22 as seen from the center position. In addition, in the configuration example shown in FIG. 3, a second sample introduction opening 24 is provided in addition to the opening 23. This sample introduction opening 24 is provided at a position facing the entrance aperture 21 on the other side of the optical axis L.

A light guide holder 210 for connection of the light guide 13 for inputting the excitation light is inserted and mounted into the entrance aperture 21. A light guide holder 220 for connection of the light guide 25 for outputting the light to be measured is inserted and mounted into the exit aperture 22. Here, illustration of the light guides 13, 25 is omitted in FIG. 3.

A sample holder fixing member 230 for fixing the sample holder 40 is mounted in the first sample introduction opening 23 (refer to FIG. 1). The sample holder 40 includes a sample container 400 with a hollow space (e.g. quadrangular prism shape) for containing the sample S, and a container supporter 401 extending from the sample container 400. The container 400 is fixed to the body 200 via the supporter 401 and the fixing member 230 while being located at the center of the integrating sphere body 200. Preferably, the sample container 400 is made of a material through which light including the excitation light and the light to be measured transmits, and an optical cell made of synthetic quartz glass is preferably used, for example. The container supporter 401 is composed of a rod-like branch pipe or the like extending in the shape of a pipe, for example. Further, a second sample holder 240 for setting the sample S is mounted in the second sample introduction opening 24 (refer to FIG. 2).

The opening 23 and the sample holder 40 can be preferably used, for example, in the case where the sample S is a solution in which a luminescent material is dissolved. Also, such a sample holder 40 can be used even in the case where the sample S is a solid sample, a powder sample, or the like. The opening 24 and the sample holder 240 can be preferably used, for example, in the case where the sample S is a solid sample or a powder sample. In this case, a sample holding substrate, a petri dish, or the like can be used as the sample container, for example.

Figure 4:
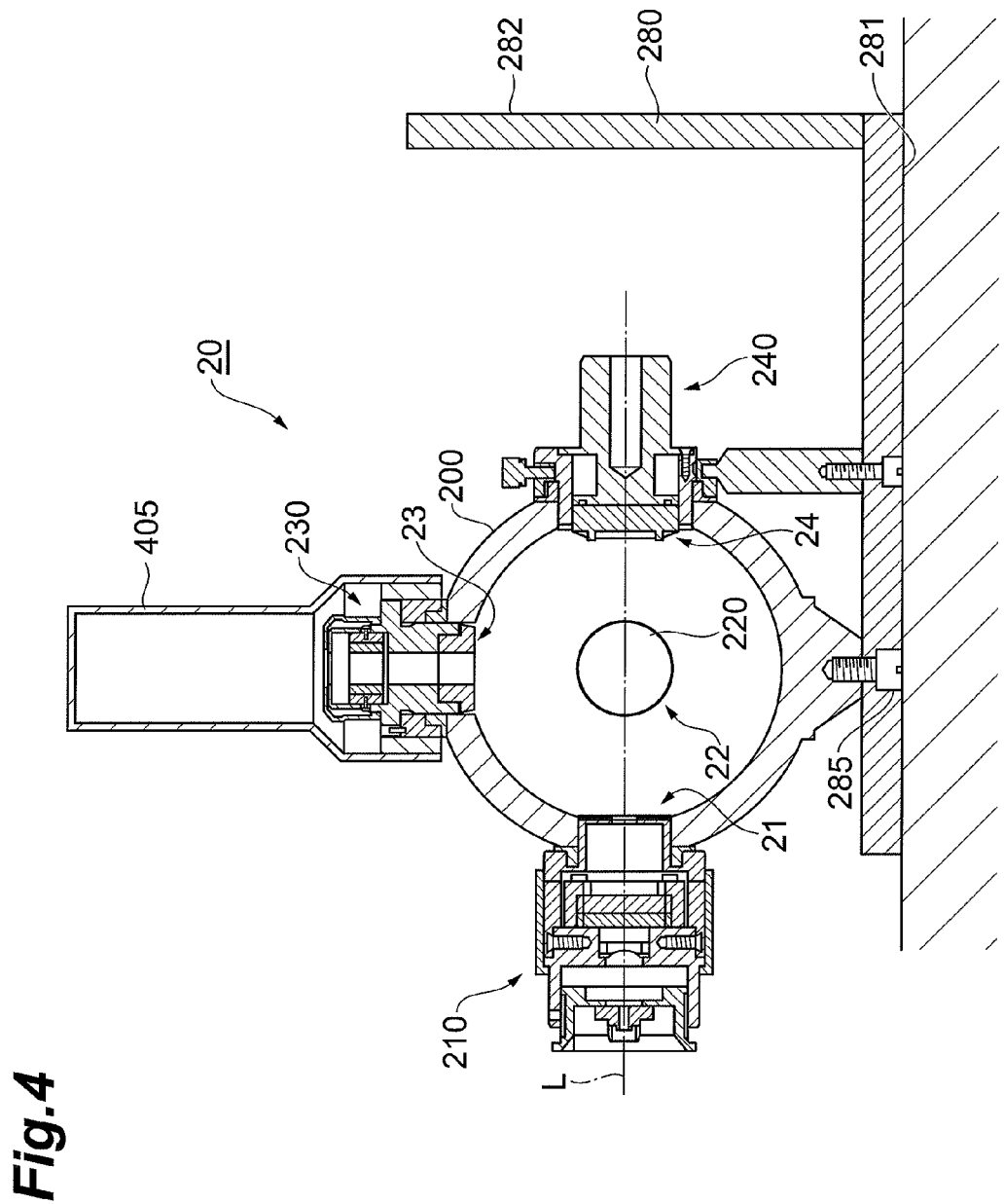
FIG. 4 is a sectional view showing an example of a configuration of the integrating sphere.

These sample holders are selectively used depending on the type of the sample S, the content of spectroscopic measurement, and the like. When the sample holder 40 is used, the integrating sphere 20 is set with the ground contact surface 281 of the mount 280 down so that the optical axis L is along a horizontal line. Also, when the sample holder 240 is used, the integrating sphere 20 is set with the ground contact surface 282 of the mount 280 down so that the optical axis L is along a vertical line. Further, when a measurement without the sample container 400 is necessary, for example, the measurement is performed with a light shielding cover 405 put on as shown in FIG. 4.

The light guide 13 for inputting the excitation light is held while being positioned by a light guide holding section 211 of the light guide holder 210. Light from the excitation light source 11 (refer to FIG. 1) is guided to the integrating sphere 20 by the light guide 13, and the sample S held in the integrating sphere 20 is irradiated with the light, while the light is collected by a condensing lens 212 placed in the light guide holder 210. Further, the light guide 25 for outputting the light to be measured is held while being positioned by the light guide holder 220.

Light from the sample S irradiated with the excitation light is multi-diffusely-reflected by high diffuse reflection powders applied on the inner wall of the integrating sphere body 200. The diffusely-reflected light enters the light guide 25 connected to the light guide holder 220, and is guided to the spectroscopic analyzer 30 as light to be measured via the light guide 25. Thus, the spectroscopic measurement of the light to be measured from the sample S is performed. The light from the sample S as the light to be measured includes: light emission such as fluorescence generated at the sample S by irradiation of the excitation light, light components of the excitation light scattered, reflected, and the like in the integrating sphere 20 without being absorbed in the sample S, and the like.

Figure 5:
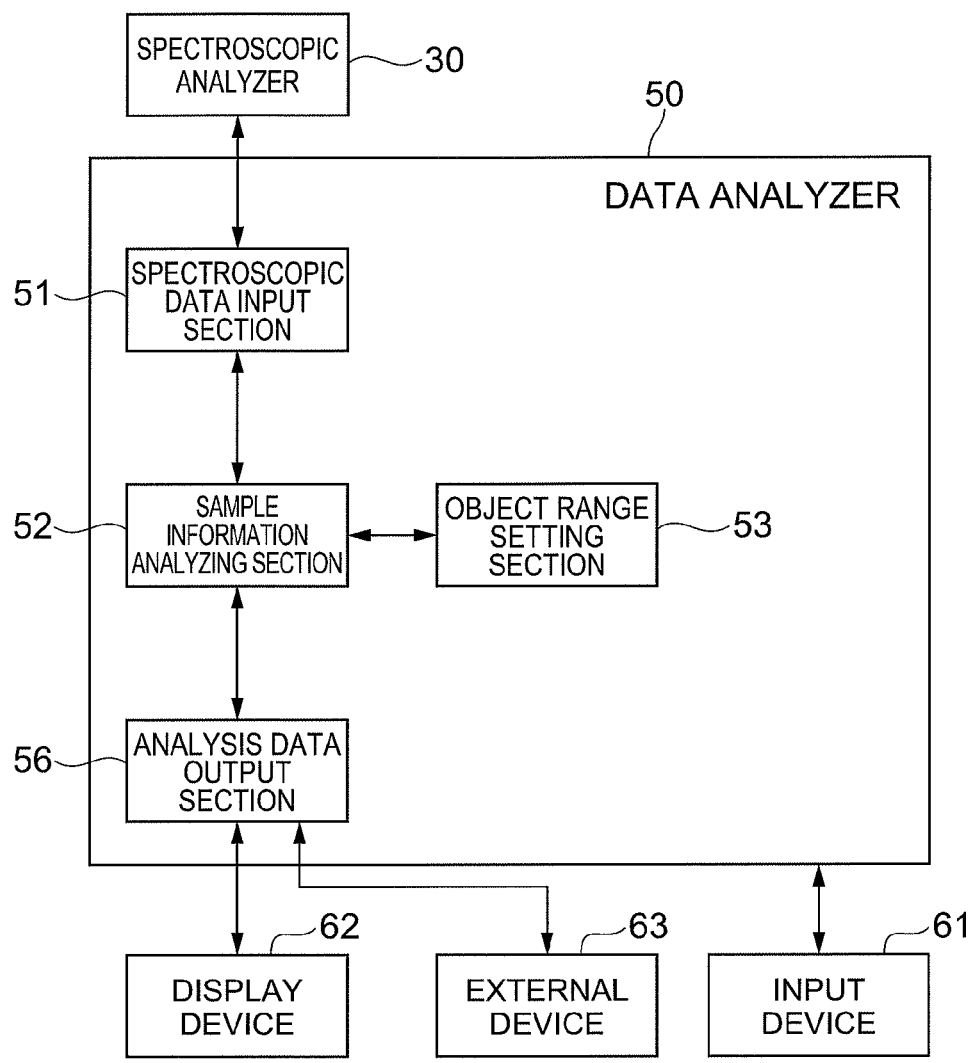
FIG. 5 is a block diagram showing an example of a configuration of a data analyzer.

FIG. 5 is a block diagram showing an example of the configuration of the data analyzer 50 used in the spectroscopic measurement apparatus 1A shown in FIG. 1. The data analyzer 50 of the present configuration example includes a spectroscopic data input section 51, a sample information analyzing section 52, an object range setting section 53, and an analysis data output section 56.

The spectroscopic data input section 51 is input means for inputting wavelength spectrum data that is spectroscopic data of the sample S obtained by the spectroscopic analyzer 30. The wavelength spectrum data input from the spectroscopic data input section 51 are sent to the sample information analyzing section 52. The sample information analyzing section 52 is sample information analyzing means which analyzes the input wavelength spectrum, and obtains information of the sample S.

The object range setting section 53 is object range setting means which sets, for the obtained wavelength spectrum, an object range being a wavelength range to be used for data analysis. Specifically, the object range setting section 53, in response to that excitation light and light emission from the sample S are included in the light to be measured, sets a first object range in a short wavelength side corresponding to the excitation light and a second object range in a long wavelength side corresponding to the light emission from the sample S and different from the first object range, of the entire measurement wavelength range in the wavelength spectrum. Such a setting of the object ranges is executed automatically by a predetermined setting algorithm, or manually based on the content of an input from the input device 61 by an operator. Further, the analyzing section 52 analyzes, for the wavelength spectrum for which object ranges have been set, the wavelength spectrum in a wavelength range including the first object range and the second object range, and thereby determines a luminescence quantum yield of the sample S.

The analysis data output section 56 is output means for outputting data indicating an analysis result in the sample information analyzing section 52. When the analysis result data by the analyzing section 52 is output via the output section 56 to the display device 62, the display device 62 displays the analysis result in a predetermined display screen to the operator. Further, the output target of the data by the output section 56 is not always the display device 62, and may be another device. In FIG. 5, in addition to the display device 62, an external device 63 is connected to the analysis data output section 56. Such an external device 63 is, for example, a printer, an external memory device, or another terminal device.

A process corresponding to the spectroscopic measurement method to be executed in the data analyzer 50 shown in FIG. 1 and FIG. 5 can be realized by the spectroscopic measurement program for making a computer execute a data analysis for the wavelength spectrum obtained by the spectroscopic analyzer 30 as spectroscopic means. For example, the data analyzer 50 can be configured with a CPU for executing respective software programs necessary for a spectroscopic measurement process, ROM for storing the software programs and the like, and RAM for storing data temporarily while running the program. In such a configuration, the CPU executes a predetermined spectroscopic measurement program, so that the data analyzer 50 and the spectroscopic measurement apparatus 1A described above can be realized.

Furthermore, the above-described program for making a CPU execute each process for spectroscopic measurement can be stored in a computer readable recording medium, and can be distributed. Such a recording medium includes, for example, magnetic media such as a hard disk and flexible disk, optical media such as a CD-ROM and DVD-ROM, magneto-optical media such as a floptical disk, or a hardware device such as a RAM, ROM, and semiconductor nonvolatile memory especially prepared so as to execute or store program instructions.

The spectroscopic measurement to be performed by the excitation light supplying section 10, the integrating sphere 20, and the spectroscopic analyzer 30 and the data analysis to be executed in the data analyzer 50 for the wavelength spectrum obtained by the spectroscopic analyzer 30 will be more specifically described.

When the luminescence quantum yield of the sample S is determined by the PL method, generally used is a method of performing a reference measurement of performing a measurement by supplying the excitation light to the interior of the integrating sphere 20 without the sample S and a sample measurement of performing a measurement by supplying the excitation light to the interior of the integrating sphere 20 with the sample S, and determining the luminescence quantum yield from the results of those two times of measurement. Specifically, the reference measurement is performed, for example, with the sample container (sample cell, sample holding substrate, or the like) without containing the sample S located in the integrating sphere 20. Also, the sample measurement is performed with the sample container containing the sample S located in the integrating sphere 20.

Figure 6:
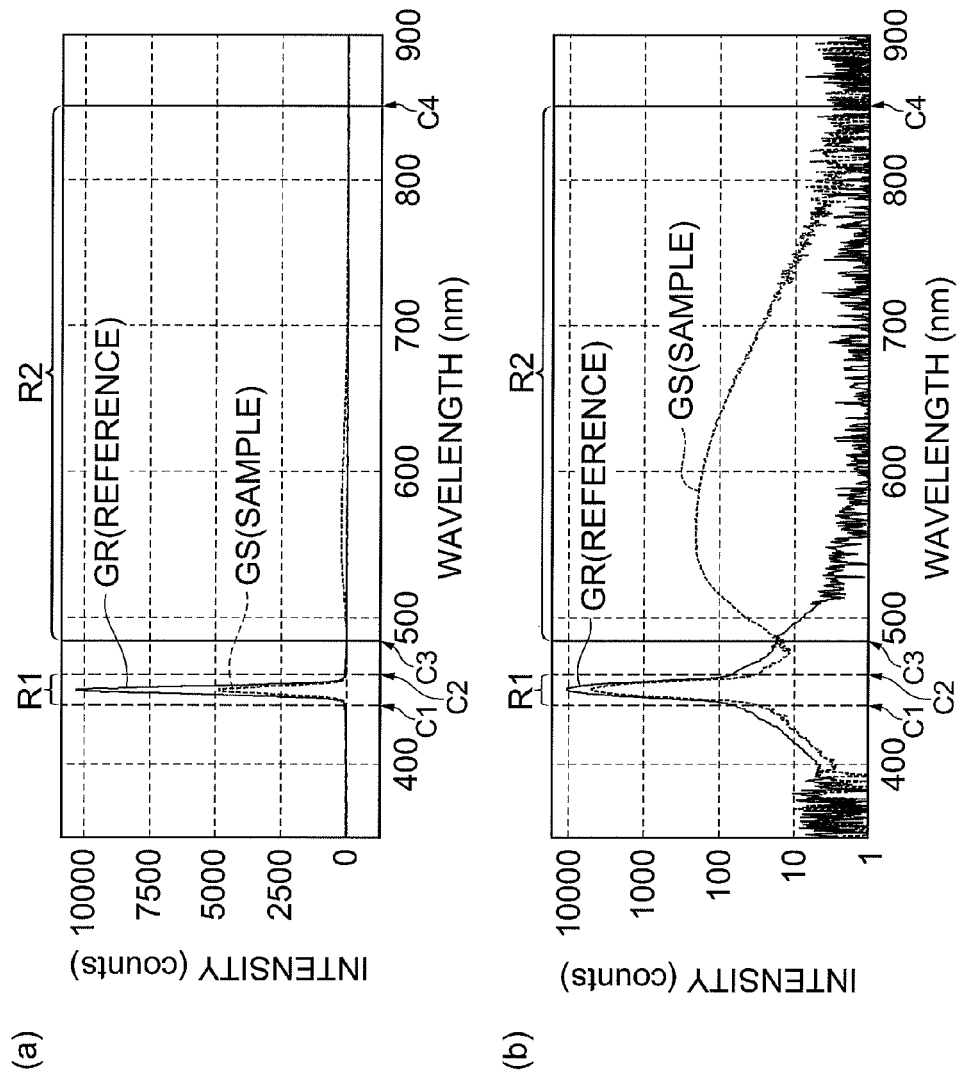
FIG. 6 includes graphs showing an example of wavelength spectra obtained by a reference measurement and a sample measurement.

FIG. 6 includes graphs showing examples of wavelength spectra obtained by a reference measurement and a sample measurement. In FIG. 6, graph (a) shows wavelength spectra with a linear scale, and graph (b) shows wavelength spectra with a log scale. Further, in the graphs (a) and (b) of FIG. 6, the graph GR shows a wavelength spectrum obtained for the excitation light by the reference measurement without the sample S. Also, the graph GS shows a wavelength spectrum of the excitation light+light emission obtained by the sample measurement with the sample S.

The object range setting section 53 of the data analyzer 50 sets, for such wavelength spectra, a first object range R1 in a short wavelength side corresponding to the excitation light and a second object range R2 in a long wavelength side corresponding to the light emission from the sample S. In the graphs of FIG. 6, a short wavelength side range end of the first object range R1 is shown as C1, and a long wavelength side range end thereof is shown as C2. Also, a short wavelength side range end of the second object range R2 is shown as C3, and a long wavelength side range end thereof is shown as C4.

Further, the sample information analyzing section 52 analyzes the wavelength spectra in a wavelength range including the object ranges R1, R2, and determines the luminescence quantum yield Φ of the sample S. Specifically, the measured intensity (excitation light intensity) in the first object range R1 obtained in the reference measurement without the sample S is set to $I_{R1}$, and the measured intensity (light emission intensity, intensity of stray light and the like of the excitation light) in the second object range R2, to $I_{R2}$, and the measured intensity in the entire measurement wavelength range of the spectroscopic analyzer 30, to $I_{R0}$. Also, the measured intensity (excitation light intensity, intensity after absorption by the sample) in the first object range R1 obtained in the sample measurement with the sample S is set to $I_{S1}$, and the measured intensity (light emission intensity) in the second object range R2, to $I_{S2}$, and the measured intensity in the entire measurement wavelength range, to $I_{S0}$. At this time, a measurement value $\Phi_0$ of the luminescence quantum yield defined by a ratio of the number of photons of light emitted from the sample S to the number of photons of excitation light absorbed by the sample S is determined by the following equation:

$$\Phi_0 = \frac{\text{the rate of photon emission}}{\text{the rate of absorption}} = \frac{I_{S2} - I_{R2}}{I_{R1} - I_{S1}} \quad \text{[Equation 1]}$$

Figure 7:
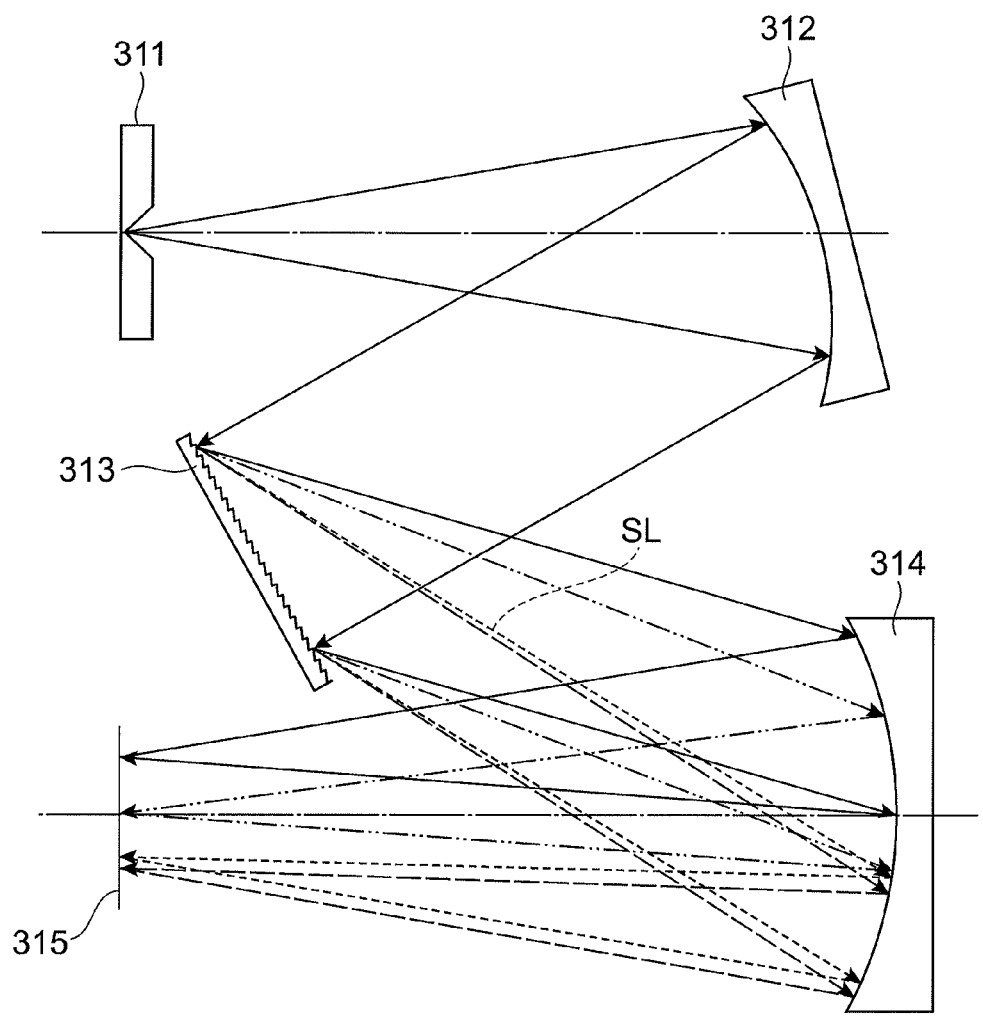
FIG. 7 is a diagram showing generation of stray light in a multi-channel spectrometer.

Here, in the spectroscopic measurement apparatus 1A using a multi-channel spectrometer in the spectroscopic analyzer 30 as shown in FIG. 1, relatively much stray light is generated due to the structure and the like of the spectrometer, and there is a problem of the effect of stray light on measurement results. FIG. 7 is a view showing generation of stray light in a multi-channel spectrometer. This multi-channel spectrometer is configured with an entrance slit 311, a collimating optical system 312, a diffraction grating 313 as a dispersive element, and a focusing optical system 314. In FIG. 7, shown is, as an example of stray light, the case where stray light SL generated at the diffraction grating 313 is output via the focusing optical system 314 at a wavelength spectrum output plane 315 as a wavelength component different from the original.

With regard to such stray light, for example, reducing the effect of stray light by a method such as increasing the size of the spectrometer can be considered. However, with such a configuration, there is a problem of complication in the structure of the spectrometer as a result of taking a measure against stray light, an increase in cost, and the like (refer to Patent Document 5: Japanese Patent Application Laid-Open No. H5-60613). Further, there is a limit to the method of physically reducing stray light as in the above, and in some cases, the effect of a reduction in stray light cannot be sufficiently obtained due to individual variability and the like of each of the spectrometers.

On the other hand, the spectroscopic measurement apparatus 1A of the above-described embodiment, in the data analysis to be executed by the data analyzer 50 for the wavelength spectra obtained in the reference measurement and the sample measurement, reduces the effect of stray light by calculation, and determines an accurate luminescence quantum yield. Specifically, for the measurement results in the reference measurement and the sample measurement, and the measurement value $\Phi_0$ of the luminescence quantum yield, the analyzing section 52 defines factors β, γ regarding stray light in the reference measurement as:

$$\beta = I_{R1}/I_{R0}$$

$$\gamma = I_{R2}/I_{R0}$$

Then, a method using these factors β, γ for determining an analysis value Φ of the luminescence quantum yield with the reduced effect of stray light by:

$$\Phi = \beta\Phi_0 + \gamma$$

is used. Here, the factor β indicates a ratio of the number of photons observed in the first object range (excitation light wavelength range) to the entire wavelength range assuming that the excitation light has spread to the entire measurement wavelength range due to stray light of the spectrometer. Also, the factor γ likewise indicates a ratio of the number of photons observed in the second object range (light emission wavelength range) to the entire wavelength range.

Figure 8:
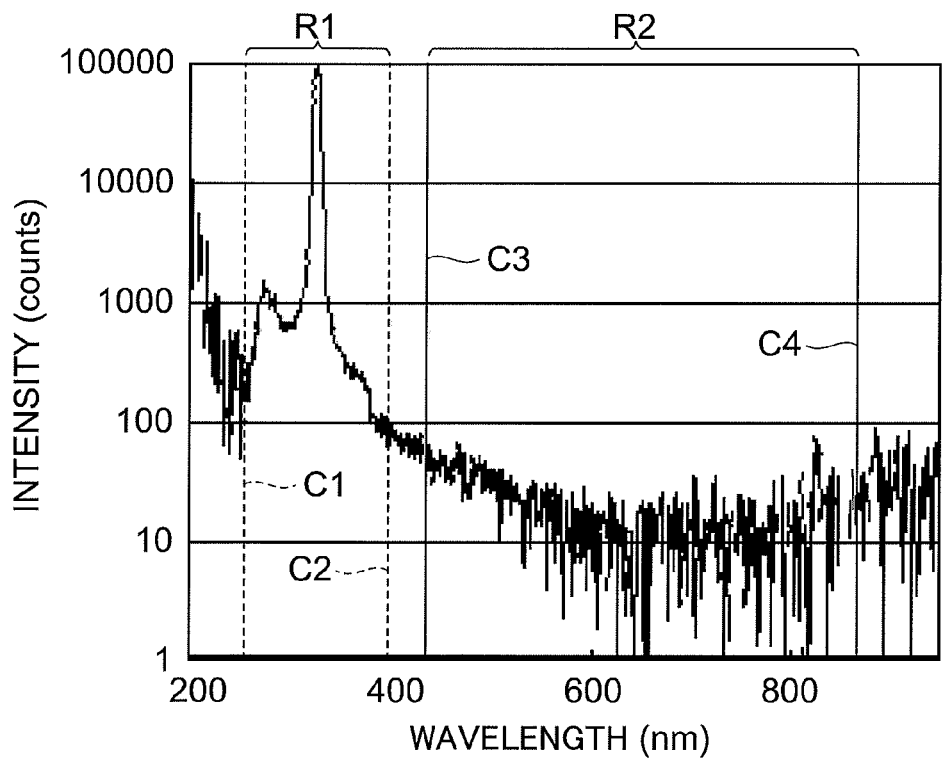
FIG. 8 is a graph showing a wavelength spectrum obtained by the reference measurement.
Figure 9:
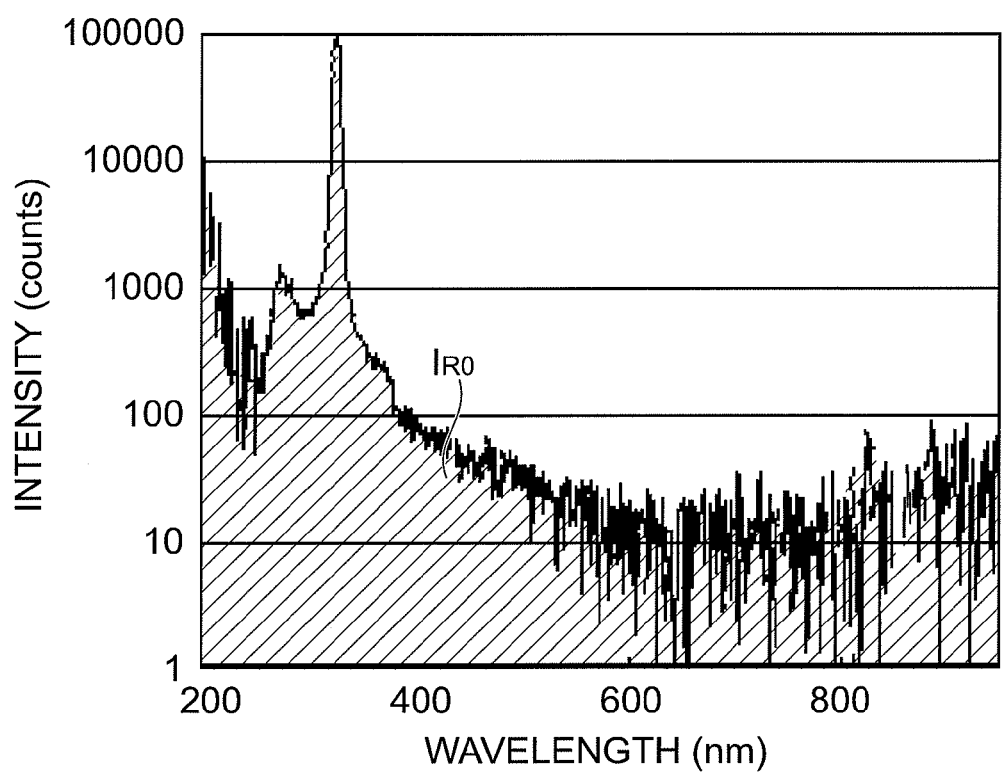
FIG. 9 is a graph showing a wavelength spectrum obtained by the reference measurement.
Figure 10:
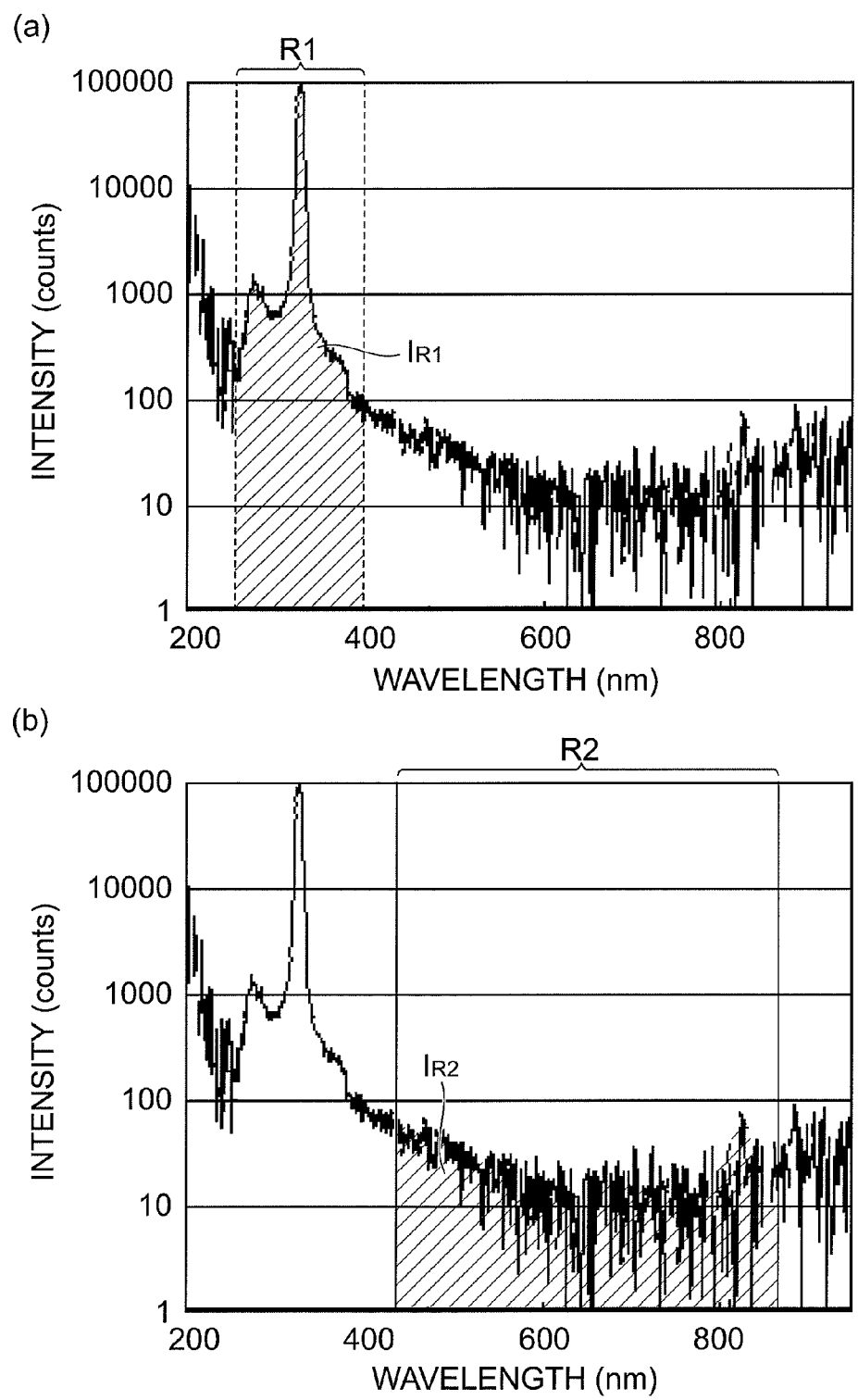
FIG. 10 includes graphs showing a wavelength spectrum obtained by the reference measurement.

Derivation of the analysis value Φ of the luminescence quantum yield will be specifically described by using the graphs of FIG. 8 to FIG. 10. FIG. 8 to FIG. 10 are graphs showing a wavelength spectrum obtained in the reference measurement of supplying the excitation light to the interior of the integrating sphere 20 without the sample S. In this example, the entire measurement wavelength range by the spectroscopic analyzer 30 is 200 nm to 950 nm. As shown in FIG. 8, for the wavelength spectrum obtained in this entire measurement wavelength range, the object range setting section 53 of the data analyzer 50 sets range ends C1, C2 of the first object range R1 corresponding to the excitation light and range ends C3, C4 of the second object range R2 corresponding to the light emission (for example, fluorescence) from the sample S. Here, in the reference measurement performed without the sample S, a light component detected in the second object range R2 is stray light or the like caused by the excitation light, for example.

For such a wavelength spectrum, the sample information analyzing section 52 calculates measured intensities in the respective wavelength ranges of the reference measurement. First, as shown in the graph of FIG. 9, a measured intensity (integrated value of the measured intensity in the wavelength range) $I_{R0}$ in the entire measurement wavelength range of the wavelength spectrum in its entirety is determined. Further, as shown in the graphs (a), (b) of FIG. 10, with regard to the first object range R1 and the second object range R2, corresponding measured intensities $I_{R1}$, $I_{R2}$ are determined, respectively. In addition, measured intensities $I_{S0}$, $I_{S1}$, $I_{S2}$ in the respective wavelength ranges of the sample measurement can also be calculated by the same method.

Further, based on these measured intensities $I_{R0}$, $I_{R1}$, $I_{R2}$ in the reference measurement, the factors $\beta=I_{R1}/I_{R0}$, $\gamma=I_{R2}/I_{R0}$ regarding stray light described above are determined. These factors for stray light correction satisfy $\beta>0$, $\gamma>0$, and $\beta+\gamma\leq 1$. Further, in the reference measurement, since most of the excitation light is considered to be detected in the first object range R1, $\beta$ takes a value close to 1, while $\gamma$ takes a value close to 0. Specifically, in the example shown in FIG. 8 to FIG. 10, $\beta=0.93$, and $\gamma=0.02$.

Here, the total intensity of the excitation light in the reference measurement is set to $I_0$ ($=I_{R0}$), the total intensity of the excitation light in the sample measurement is set to $I_1$, the total intensity of the fluorescence in the sample measurement is set to F, and the true value of the luminescence quantum yield of the sample S is set to $\Phi$. Further, where the excitation light transmittance in the sample S is $\alpha$, the transmittance $\alpha$ is determined by:

$$\alpha = I_1/I_0$$

When there is no influence of stray light in the reference measurement and the sample measurement, and the factors regarding stray light are $\beta=1$ and $\gamma=0$, the value $\Phi$ of the luminescence quantum yield of the sample S is accurately determined by:

$$\Phi = \frac{F}{I_0 - I_1} = \frac{F}{(1-\alpha)I_0} \quad \text{[Equation 2]}$$

In an actual measurement, due to the effect of stray light generated in the spectrometer, the factor $\gamma$ does not become 0. At this time, the excitation light intensity $I_{R1}$ and the fluorescence intensity $I_{R2}$ in the reference measurement and the excitation light intensity $I_{S1}$ and the fluorescence intensity $I_{S2}$ in the sample measurement respectively become:

$$I_{R1} = \beta I_0$$

$$I_{R2} = \gamma I_0$$

$$I_{S1} = \beta I_1 = \alpha\beta I_0$$

$$I_{S2} = F + \gamma I_1 = F + \alpha\gamma I_0$$

Further, the measurement value $\Phi_0$ of the luminescence quantum yield determined from these measured intensities becomes:

$$\Phi_0 = \frac{I_{S2} - I_{R2}}{I_{R1} - I_{S1}} \quad \text{[Equation 3]}$$

$$= \frac{F + \alpha\gamma I_0 - \gamma I_0}{\beta I_0 - \alpha\beta I_0}$$

$$= \frac{F}{\beta(1-\alpha)I_0} + \frac{\gamma(\alpha-1)I_0}{\beta(1-\alpha)I_0}$$

$$= \frac{1}{\beta}\Phi - \frac{\gamma}{\beta}$$

In this equation, the first term of $\Phi/\beta$ indicates that the luminescence quantum yield is calculated larger by $1/\beta (\geq 1)$ times since the number of photons of excitation light absorbed by the sample S is measured smaller under the effect of stray light. Further, the second term of $-\gamma/\beta$ can be considered as an error provided by background subtraction of fluorescence.

In the measurement value $\Phi_0$ of the luminescence quantum yield described above, if the effect of stray light is small, and $\beta$ becomes 1, and $\gamma$ becomes 0, the measurement value $\Phi_0$ becomes $\Phi$ with respect to the true value $\Phi$ of the luminescence quantum yield. Further, when a reduction of the effect of stray light by correction is necessary, by using the following equation obtained by inversely solving the above-described equation, $$\Phi = \beta\Phi_0 + \gamma \quad \text{[Equation 4]}$$

the analysis value $\Phi$ corresponding to the true value of the luminescence quantum yield can be determined.

Effects of the spectroscopic measurement apparatus, spectroscopic measurement method, and spectroscopic measurement program according to the above-described embodiment are described.

In the spectroscopic measurement apparatus 1A, the measurement method, and the measurement program shown in FIG. 1 to FIG. 10, the spectroscopic measurement apparatus 1A includes the integrating sphere 20 which has the aperture 21 for entrance of the excitation light and the aperture 22 for exit of the light to be measured and is configured so as to be capable of measurement by the PL method, and the spectroscopic analyzer 30 which performs spectroscopic measurement of the light to be measured so that the excitation light and the light emission from the sample S can be separated by the wavelength spectrum.

Then, in analysis of sample information using the wavelength spectrum, the results of two times of measurement of the reference measurement without the sample S and the sample measurement with the sample S are used, and for the measurement value $\Phi_0$ of the luminescence quantum yield, the factors $\beta=I_{R1}/I_{R0}$, $\gamma=I_{R2}/I_{R0}$ regarding stray light are defined from the result of the reference measurement, and the analysis value $\Phi$ of the luminescence quantum yield is determined by using these factors by the calculation formula $\Phi = \beta\Phi_0 + \gamma$.

In accordance with such a configuration, by correcting the measurement value $\Phi_0$ with the above-described formula, and determining the analysis value $\Phi$ equal to the true value of the luminescence quantum yield, it becomes possible to reliably reduce the effect of stray light in the spectrometer contained in the measurement results. Particularly, in such a configuration, without performing correction or the like of the spectrum waveform by a stray light elimination, the effect of stray light is reduced by calculation in the data analysis for the wavelength spectrum, and the luminescence quantum yield can be simply and accurately determined. Further, since it is not necessary to eliminate stray light by an improvement or the like of the spectrometer, a spectroscopic measurement apparatus can be realized at low cost. Further, it is also possible to use the configuration of reducing the effect of stray light by calculation as described above together with a configuration of physically reducing stray light.

Further, the spectroscopic means for obtaining a wavelength spectrum of light to be measured is, as mentioned above regarding the spectroscopic analyzer 30, preferably a configuration including a multi-channel spectrometer having a spectrometer and a photodetector having detecting sections of multi-channels. In this case, it becomes possible to simultaneously perform measurement, in the entire wavelength range necessary for spectroscopic measurement of the excitation light and the light emission from the sample S, without performing scanning or the like of the wavelength. Further, in accordance with the above-described method of determining the analysis value $\Phi$ corrected by the factors $\beta$, $\gamma$, even in the configuration using a multi-channel spectrometer where relatively much stray light is generated as described above, the luminescence quantum yield with the reduced effect of stray light can be preferably determined. Further, such a method can also be likewise effectively applied when a spectrometer of a configuration other than that of a multi-channel spectrometer is used.

Here, there is a description of eliminating the effect of stray light in a spectrophotometer in Patent Document 4 (Japanese Patent Application Laid-Open No. H11-30552). However, in the configuration described in Document 4, used is a method of separately preparing, for the spectrophotometer, reference light outputting means including a reference spectrometer, and thereby estimating the effect of stray light as an apparatus constant. In such a configuration, it is necessary to correct stray light through many steps, and the configuration of a spectroscopic measurement apparatus and a measurement method including stray light correction are both complicated. On the other hand, in the spectroscopic measurement apparatus 1A of the above-described embodiment, by defining the factors $\beta$, $\gamma$ by using the measured intensities respectively in the first object range R1 corresponding to the excitation light and the second object range R2 corresponding to the light emission from the sample S, and reducing the effect of stray light by calculation, derivation of the luminescence quantum yield can be simply and accurately performed.

A specific example of a spectroscopic measurement method to be performed in the spectroscopic measurement apparatus 1A shown in FIG. 1 will be described with reference to FIG. 11 and FIG. 12.

Figure 11:
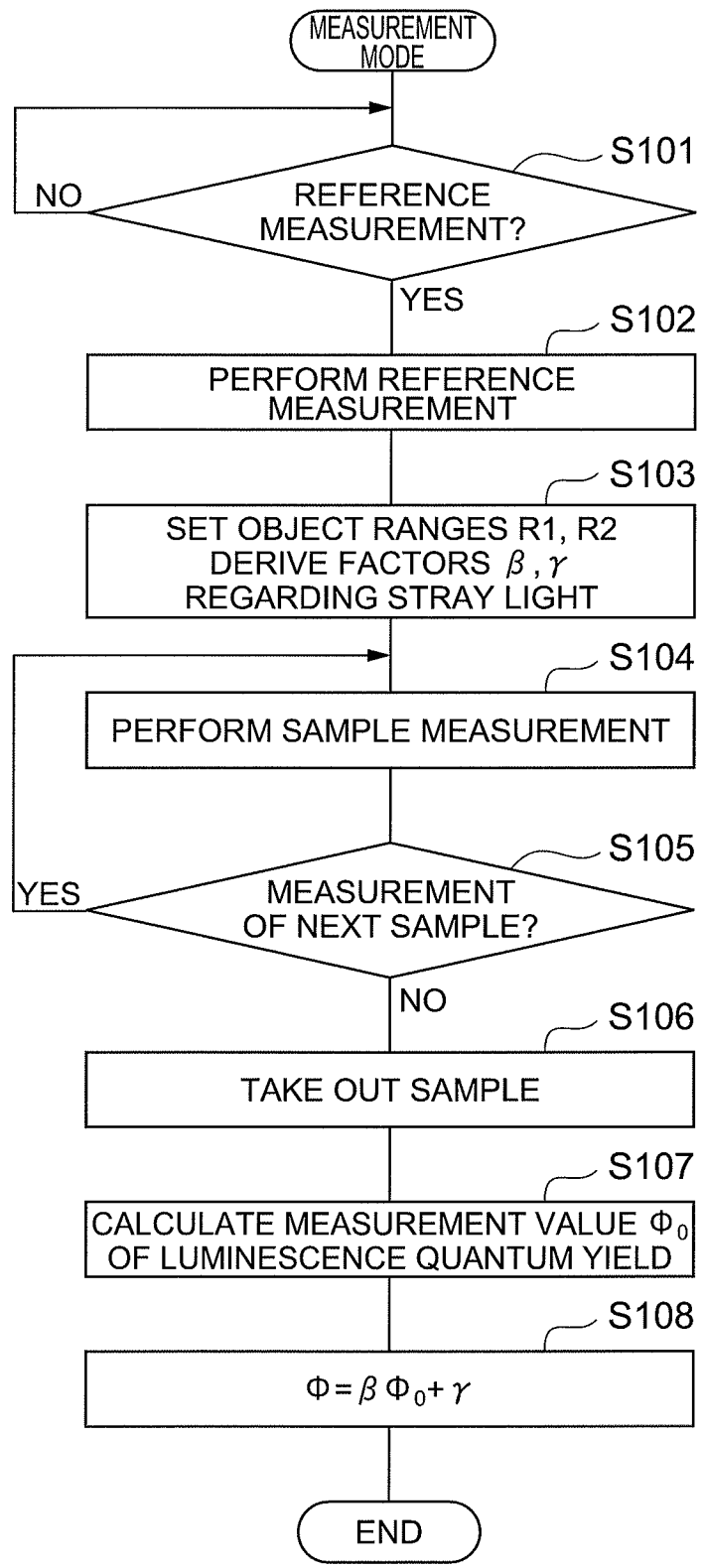
FIG. 11 is a flowchart showing an operation example of the spectroscopic measurement apparatus in a measurement mode.

FIG. 11 is a flowchart showing an operation example of the spectroscopic measurement apparatus in a measurement mode. In this operation example of the measurement mode, first, it is confirmed whether to start a reference measurement without the sample S (step S101), and the reference measurement is performed if a measurement start has been instructed, to obtain a wavelength spectrum (S102). Further, setting of first and second object ranges R1, R2 and derivation of factors $\beta$, $\gamma$ regarding stray light are performed for the wavelength spectrum of the reference measurement (S103). In addition, the setting of object ranges and derivation of factors may be performed together with calculation of the luminescence quantum yield after execution of a sample measurement.

Next, the sample S of a measurement object is set in the sample holder of the integrating sphere 20, and a sample measurement with the sample S is performed, to obtain a wavelength spectrum (S104). Subsequently, it is confirmed whether to perform measurement for the next sample S (S105), and step S104 is repeatedly executed when the measurement is performed. When all the measurements of the samples S are finished, the sample S for which measurement has been finished is taken out of the integrating sphere 20 (S106).

When the spectroscopic measurement of the sample S is finished, data analysis necessary for determining the luminescence quantum yield is performed for the wavelength spectra obtained by the reference measurement and the sample measurement. In this example, the measurement value $\Phi_0$ of the luminescence quantum yield is calculated, by the foregoing method, from the measured intensities in the respective wavelength ranges in the wavelength spectra obtained by the reference and sample measurements (S107). Then, the analysis value $\Phi$ equal to the true value of the luminescence quantum yield is determined, by using the factors $\beta$, $\gamma$ derived in step S103, by an equation $\Phi=\beta\Phi_0+\gamma$ (S108). With the above, the spectroscopic measurement of the sample S and derivation of the luminescence quantum yield in the measurement mode ends.

Figure 12:
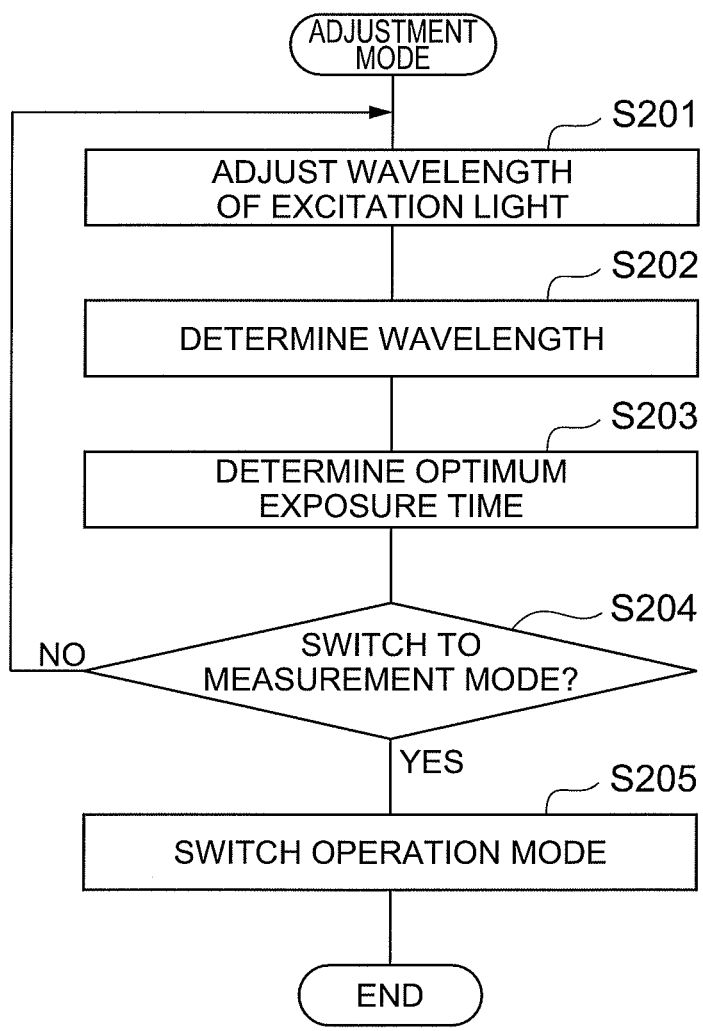
FIG. 12 is a flowchart showing an operation example of the spectroscopic measurement apparatus in an adjustment mode.

FIG. 12 is a flowchart showing an operation example of the spectroscopic measurement apparatus in an adjustment mode. Such an adjustment mode is, for example, in the configuration using the wavelength selecting section 12 such as a spectrometer in the excitation light supplying section 10 as shown in FIG. 1, used for setting the irradiation condition of the excitation light.

In this operation example of the adjustment mode, first, the wavelength of the excitation light is adjusted by adjusting the setting of the wavelength selecting section 12 or the like (S201), to determine its wavelength (S202). Next, with reference to the characteristics and the like of the set excitation light, an optimum exposure time during which the sample S is irradiated with the excitation light is determined (S203). Subsequently, it is confirmed whether to switch the operation mode of the spectroscopic measurement apparatus from the adjustment mode to the measurement mode (S204), and the operation mode is switched to the measurement mode if the switching is instructed (S205). If the switching is not instructed, the setting of the irradiation condition of the excitation light is repeatedly executed.

Here, in a quantum yield measurement, light components such as excitation light, light emission, and fluorescence are measured in a reference measurement and a sample measurement as mentioned above, and these light components have respectively different light distribution characteristics. Therefore, in a quantum yield measurement using a fluorophotometer or the like, it is difficult to completely capture and guide those light components to be measured to a detector. With respect to this, in the above-described spectroscopic measurement apparatus using an integrating sphere, it is possible to perform a reference measurement and a sample measurement under the same conditions, and the above-described method of determining an analysis value $\Phi$ of the luminescence quantum yield by a correction formula $\Phi=\beta\Phi_0+\gamma$ can be said to be a method suitable for such a measurement apparatus.

The spectroscopic measurement apparatus, spectroscopic measurement method, and spectroscopic measurement program according to the present invention are not limited to the above-described embodiments and configuration examples, and can be modified in many ways. For example, the integrating sphere 20 shown in FIG. 3 and FIG. 4 shows an example of an integrating sphere used in a spectroscopic measurement for a sample S, and various configurations can be specifically used. Further, the specific procedures of a spectroscopic measurement are also not limited to those in the operation examples shown in FIG. 11 and FIG. 12, and a spectroscopic measurement can be specifically performed by various procedures.

INDUSTRIAL APPLICABILITY

The present invention can be used as a spectroscopic measurement apparatus, a measurement method, and a measurement program which can reduce the effect of stray light generated in a spectrometer.

REFERENCE SIGNS LIST

1A—spectroscopic measurement apparatus, 10—excitation light supplying section, 11—excitation light source, 12—wavelength selecting section, 13—light guide, 14—optical filter, 20—integrating sphere, 200—integrating sphere body, 21—entrance aperture, 210—light guide holder, 22—exit aperture, 220—light guide holder, 23, 24—sample introduction opening, 230—sample holder fixing member, 240—sample holder, 25—light guide, 30—spectroscopic analyzer, 31—spectroscopic section, 32—spectroscopic data generating section, 40—sample holder, 400—sample container, 401—container supporter, 405—light shielding cover, 50—data analyzer, 51—spectroscopic data input section, 52—sample information analyzing section, 53—object range setting section, 56—analysis data output section, 61—input device, 62—display device, 63—external device.

The invention claimed is:

1. A spectroscopic measurement apparatus comprising:
an integrating sphere in which a sample as a measurement object is located, and having an entrance aperture for inputting excitation light with which the sample is irradiated, and an exit aperture for outputting light to be measured from the sample;
spectroscopic means dispersing the light to be measured output from the exit aperture of the integrating sphere and obtaining a wavelength spectrum; and
data analyzing means performing data analysis of the wavelength spectrum obtained by the spectroscopic means,
the data analyzing means including:
object range setting means setting, of an entire measurement wavelength range in the wavelength spectrum, a first object range corresponding to the excitation light and a second object range which is a wavelength range corresponding to light emission from the sample and different from the first object range; and
sample information analyzing means determining a luminescence quantum yield of the sample by analyzing the wavelength spectrum in a wavelength range including the first object range and the second object range,
wherein the sample information analyzing means,
when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and
a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$,
determines a measurement value $\Phi_0$ of the luminescence quantum yield by:

$$\Phi_0 = (I_{S2} - I_{R2})/(I_{R1} - I_{S1}),$$

defines factors $\beta$, $\gamma$ regarding stray light in the reference measurement as:

$$\beta = I_{R1}/I_{R0}$$

$$\gamma = I_{R2}/I_{R0}, \text{ and}$$

determines an analysis value $\Phi$ of the luminescence quantum yield by:

$$\Phi = \beta \Phi_0 + \gamma.$$

2. The spectroscopic measurement apparatus according to claim 1, wherein the spectroscopic means includes a spectrometer for dispersing the light to be measured into wavelength components and a photodetector having detecting sections of multi-channels for detecting respective wavelength components of the light to be measured dispersed by the spectrometer, and is configured as a multi-channel spectrometer.

3. A spectroscopic measurement method using a spectroscopic measurement apparatus including an integrating sphere in which a sample as a measurement object is located, and having an entrance aperture for inputting excitation light with which the sample is irradiated, and an exit aperture for outputting light to be measured from the sample, and spectroscopic means dispersing the light to be measured output from the exit aperture of the integrating sphere and obtaining a wavelength spectrum, for performing data analysis of the wavelength spectrum obtained by the spectroscopic means, the spectroscopic measurement method comprising:
an object range setting step of setting, of an entire measurement wavelength range in the wavelength spectrum, a first object range corresponding to the excitation light and a second object range which is a wavelength range corresponding to light emission from the sample and different from the first object range; and
a sample information analyzing step of determining a luminescence quantum yield of the sample by analyzing the wavelength spectrum in a wavelength range including the first object range and the second object range,
wherein the sample information analyzing step,
when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and
a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$,
determines a measurement value $\Phi_0$ of the luminescence quantum yield by:

$$\Phi_0 = (I_{S2} - I_{R2})/(I_{R1} - I_{S1}),$$

defines factors $\beta$, $\gamma$ regarding stray light in the reference measurement as:

$$\beta = I_{R1}/I_{R0}$$

$$\gamma = I_{R2}/I_{R0}, \text{ and}$$

determines an analysis value $\Phi$ of the luminescence quantum yield by:

$$\Phi = \beta \Phi_0 + \gamma.$$

4. The spectroscopic measurement method according to claim 3, wherein the spectroscopic means includes a spectrometer for dispersing the light to be measured into wavelength components and a photodetector having detecting sections of multi-channels for detecting respective wavelength components of the light to be measured dispersed by the spectrometer, and is configured as a multi-channel spectrometer.

5. A spectroscopic measurement program being applied to a spectroscopic measurement apparatus including an integrating sphere in which a sample as a measurement object is located, and having an entrance aperture for inputting excitation light with which the sample is irradiated, and an exit aperture for outputting light to be measured from the sample, and spectroscopic means dispersing the light to be measured output from the exit aperture of the integrating sphere and obtaining a wavelength spectrum, for making a computer execute data analysis of the wavelength spectrum obtained by the spectroscopic means, the program making the computer execute:

an object range setting process of setting, of an entire measurement wavelength range in the wavelength spectrum, a first object range corresponding to the excitation light and a second object range which is a wavelength range corresponding to light emission from the sample and different from the first object range; and a sample information analyzing process of determining a luminescence quantum yield of the sample by analyzing the wavelength spectrum in a wavelength range including the first object range and the second object range, wherein the sample information analyzing process, when a measured intensity in the first object range obtained in a reference measurement of performing a measurement by supplying the excitation light to the interior of the integrating sphere without the sample is set to $I_{R1}$, and a measured intensity in the second object range, to $I_{R2}$, and a measured intensity in the entire measurement wavelength range, to $I_{R0}$, and a measured intensity in the first object range obtained in a sample measurement of performing a measurement by supplying the excitation light to the interior of the integrating sphere with the sample is set to $I_{S1}$, and a measured intensity in the second object range, to $I_{S2}$, and a measured intensity in the entire measurement wavelength range, to $I_{S0}$, determines a measurement value $\Phi_0$ of the luminescence quantum yield by:

$$\Phi_0 = (I_{S2} - I_{R2})/(I_{R1} - I_{S1}),$$

defines factors $\beta$, $\gamma$ regarding stray light in the reference measurement as:

$$\beta = I_{R1}/I_{R0}$$

$$\gamma = I_{R2}/I_{R0}, \text{ and}$$

determines an analysis value $\Phi$ of the luminescence quantum yield by:

$$\Phi = \beta \Phi_0 + \gamma.$$

6. The spectroscopic measurement program according to claim 5, wherein the spectroscopic means includes a spectrometer for dispersing the light to be measured into wavelength components and a photodetector having detecting sections of multi-channels for detecting respective wavelength components of the light to be measured dispersed by the spectrometer, and is configured as a multi-channel spectrometer.

* * * * *